United States Patent [19]

Witteles

[11] Patent Number: 4,483,341
[45] Date of Patent: Nov. 20, 1984

[54] THERAPEUTIC HYPOTHERMIA INSTRUMENT

[75] Inventor: Eleonora M. Witteles, Rancho Palos Verdes, Calif.

[73] Assignee: Atlantic Richfield Company, Los Angeles, Calif.

[21] Appl. No.: 448,114

[22] Filed: Dec. 9, 1982

[51] Int. Cl.$^3$ .............................................. A61F 7/00
[52] U.S. Cl. ................................ 128/402; 128/303.1; 128/784; 62/3
[58] Field of Search ..................... 128/303.1, 399–403, 128/DIG. 27, 784; 62/3, 335

[56] References Cited

U.S. PATENT DOCUMENTS

| | | | |
|---|---|---|---|
| 3,090,206 | 5/1963 | Arders | 62/3 |
| 3,133,539 | 5/1964 | Eidus . | |
| 3,136,134 | 6/1964 | Smith | 62/3 |
| 3,207,159 | 9/1965 | Tateisi . | |
| 3,224,206 | 12/1965 | Sizelouc | 62/3 |
| 3,282,267 | 11/1966 | Eidus . | |
| 3,327,713 | 6/1967 | Eidus | 128/303.1 |
| 3,369,549 | 2/1968 | Armao . | |
| 3,547,705 | 12/1970 | Heard | 62/3 |
| 3,941,135 | 3/1976 | von Sturm et al. | 128/784 |

OTHER PUBLICATIONS

J. R. Madigan, et al., "A Hybrid Peltier–Ettingshausen Cooler for Cryogenic Temperatures," *Solid–State Electronics*, vol. 7, pp. 643–654 (1964).

Robert J. Carpenter, III, M.D., et al., "Cryosurgery: Theory and Application to Head and Neck Neoplasia," *Head & Neck Surgery*, Nov. Dec. 1979.

Dr. Rudolf B. Horst, et al., "Application of Solid State Cooling to Spaceborne Infrared Focal Planes," 3rd International Conference on Thermoelectric Energy Conversion, U. of Texas, Arlington, Texas, Mar. 1980, IEEE.

Peter Mazur, "Theoretical and Experimental Effects of Cooling and Warming Velocity on the Survival of Frozen and Thawed Cells," *Cryobiology*, vol. 2, No. 4 (1966).

H. Bryan Neel, III, M.D., et al., "Experimental Evaluation of in situ Oncocide For Primary Tumor Therapy: Comparison of Tumor–Specific Immunity After Complete Excision, Cryonecrosis and Ligation," *The Laryngoscope*, pp. 376–387.

Dean C. Jeutter, "A Transcutaneous Implanted Battery Recharging and Biotelemeter Power Switching System," IEEE, pp. 314–321 (1982).

H. Bryan Neel, III, M.D., et al., "Cryosurgery of Respiratory Structures, I. Cryonecrosis of Trachea and Bronchus", *The Laryngoscope*, 83, pp. 1062–1071 (1973).

*Primary Examiner*—Edward M. Coven
*Assistant Examiner*—Max F. Hindenburg
*Attorney, Agent, or Firm*—Nilsson, Robbins, Dalgarn, Berliner, Carson & Wurst

[57] ABSTRACT

An implantable hypothermia instrument for the in-situ treatment of oncological disorders includes a cylindrical casing terminating at a first end in a concave tumor-abutting portion of a thermoconductive material which is thermally adjacent the cold junction of a cascaded three-component solid state cooler and shaped to partially surround the target tissue in order to provide a convergent freezing effect. The cooler comprises a thermoelectric first cooling section, a thermomagnetic second cooling section and an Ettingshausen third cooling section connected thermally in parallel to afford a stepped temperature reduction across a wide thermal gradient and to provide a temperature level, freezing rate and repetitive freeze/thaw cycles sufficient for tumor necrosis.

11 Claims, 6 Drawing Figures

THERAPEUTIC HYPOTHERMIA INSTRUMENT

BACKGROUND OF THE INVENTION

This invention relates generally to an instrument for use in cryogenic treatment of portions of the human body, and more particularly to a capsule having a solid state heat exchange means therein for the cryogenic treatment of tissue.

In the treatment of human diseases, particularly cancer, it is frequently desired to eliminate neoplastic tissue. This can be accomplished by extirpative surgery or by in-situ necrosis. Surgical intervention has the disadvantage of causing substantial metastasis by allowing the release of malignant cells into healthy tissue during the procedure. In addition, there are many instances where surgery is impossible.

A number of procedures are available for in situ necrosis. Among these are radiation therapy, chemotherapy, electrocoagulation, hyperthermia, microwave radiation and hypothermia. The primary disadvantage of these procedures as they are practiced today is the severe side effects which they may induce as well as the danger of damage to healthy tissue.

Cryosurgery, i.e., the controlled destruction of tissue by freezing for the treatment of tumors, began with the use of carbon dioxide snow and iced saline on advanced tumors. Thereafter, liquid nitrogen, applied with a cotton swab, was used for the treatment of skin cancer. More recently, a closed-tip cryosurgical unit was developed, in which the temperature of the probe tip is reduced to $-190°$ C. through the circulation of liquid nitrogen through the probe tip of a vacuum insulated tube. A second technique involves the spraying of liquid nitrogen directly onto the target area. While the closed system has the advantage of a precise localized freezing point which allows for the preservation of adjacent tissue, and the open system allows maximal freezing of the target area, both systems may be used only once with respect to internal tumors, i.e. during the surgical procedure. As a result they can only be applied to superficial carcinomas without repeated surgery. Moreover, the use of a probe produces an unfocused sphere of frozen tissue which damages healthy tissue at least as much as tumor tissue when the probe is placed adjacent to the tumor. Invasion of the tumor with the probe, i.e. freezing from the inside out, produces an increased risk of metastasis comparable to extirpative surgery.

As the temperature of a biologic system is lowered, a phase change occurs as water is converted into ice. The ice crystals which are first formed are pure water, and the formation of these crystals in the liquid phase leads to an increasing solute concentration. The liquid phase persists until the freezing point of the concentrated electrolyte solution is reached e.g. $-21°$ C. (252° K.) for a sodium chloride system.

Rapid cooling, e.g. at a rate faster than 100° C. per minute, causes intracellular ice crystals, as the water does not have a chance to leave the cell before freezing occurs As a result of such rapid freezing, small ice crystals form in the cytoplasm nucleus and mitochondria of the cell and cause uncoupling of enzyme systems and DNA damage. Rapid heat loss, as well as the pH change caused by the increasing solute concentration, also damages cellular protein leading to the denaturation and detachment of the lipoprotein complex that comprises the cell membrane. In contrast, slow cooling e.g. 1° C. to 10° C. per minute allows extra cellular ice formation while the cell membrane acts as a barrier to crystal extension into the cell. In this case, cell damage is caused solely by dehydration and toxic levels of solute concentration in the cell. Thus, the more rapid the freeze, the greater the cell damage.

A second parameter which determines the extent of cell destruction is the rate of thaw. A slow or spontaneous thaw begins with the melting of microcrystals absorbing, in phase transition, an amount of heat equal to the latent heat of crystallization i.e. 80 Cal/g $H_2O$, lowering the temperature and allowing recrystallization to occur. Thus, the microcrystals grow in size and cause increasing physical damage to the cell. Thus, slow or spontaneous thawing provides greater cell damage. Mazur, "Cryobiology" 2:181–192, 1966.

It is generally accepted that the eutectic temperature of the solution is the minimum temperature for adequate cell destruction e.g. in a physiological sodium chloride system $-21°$ C.(252° K.). However, lower temperatures are known to be more desirable and tumor control is increased by freezing tissue to at least $-60°$ C. Neel et al. "Laryngoscope", 83:1062–1071, 1973. It should be noted that there is a difference between the temperature $T_c$ on the surface of the freezing instrument and the temperature $T_n$ which is the temperature of the cell during necrosis. The difference between the $T_c$ and $T_n$ is a function of the distance from the surface of the instrument to the depth of the tissue when necrosis is to take place. It is also a function of the type of tissue treated.

One of the most important considerations in the hypothermic treatment of cancer is the vascularity of tumors and the relation of the rate of blood profusion to heat transfer. It is known that tumors have impaired blood circulation and reduced heat transfer capabilities. A tumor expands predominantly by the growth of cells at the advancing margins, where new capillaries are formed which are closely related to their conjunctive arteries and veins. Capillaries in the center of the tumor, on the other hand, are connected only to other capillaries and thus blood flow becomes quite sluggish. The application of freezing temperatures to the margin of the advancing tumor substantially diminishes the blood flow and reduces the circulatory input of heat into the target area. This reduction in heat input allows a greater volume of tissue to be frozen using repetitive freeze-thaw cycles. The cytostatic damage caused by repetitive freezes is greater than damage caused by a single freeze-thaw cycle and thus tumor control is increased.

U.S. Pat. No. 3,133,539 to Eidus describes a thermoelectric medical instrument which may be used to supply controlled cooling temperatures to the heart during surgery and for external uses such as freezing treatment of warts and skin blemishes. The instrument includes a thermocouple assembly composed of a series of semiconductor elements of the p-type, alternating with semiconductor elements of the n-type and adapted to produce cooling by the Peltier effect. The instrument of the U.S. Pat. No. 3,133,539 is of substantial size and is intended to produce a temperature approximating that of crushed ice. In fact, the maximum cooling effect at the headpiece of the instrument is disclose as being between $-20°$ C. and $-25°$ C.

U.S. Pat. No. 3,369,549 to Armao relates to a thermoelectric heat exchange capsule probe, similarly employing the Peltier effect, which may be used during surgery to freeze tumors to avoid the metastisizing for release of malignant cells into healthy tissue. Cooling of the diseased portion renders the malignant cells immobile by inhibiting the movement of fluids and cells in the tissue. It is acknowledged that freezing at sufficiently low temperatures will destroy cancer cells, but the thermoelectric instrument of the U.S. Pat. No. 3,369,549 claims only to freeze the tissue sufficiently to prohibit metastasis and the instrument is to be used as an adjunct in extirpative surgery rather than a primary instrument for cell necrosis.

Solid state cooling devices, such as those shown in the aforementioned patents, have heretofore been unable to attain the cytostatic temperatures required for cell necrosis and tumor control. The efficiency of the Peltier cooler, in terms of temperature change per unit of electric current required, decreases dramatically with colder temperatures. Even with cascaded thermoelectric coolers, $-90°$ C. from room temperature is the practical limit with the Peltier effect, and the maximum temperature difference developed across a stage is directly proportional to the square of the cold junction temperature. Thus, it is apparent that solid state cooling devices of efficacious size and current demands, while capable of providing substantial advantages over closed tip liquid nitrogen cryoprobes, have heretofore been incapable of obtaining the extreme subfreezing temperatures required for effective tumor control.

SUMMARY OF THE INVENTION

In accordance with the present invention, a hypothermia instrument is provided for the application of cytostatic freezing temperatures to selected portions of the body, the instrument comprising an outer casing of substantially rigid material; an outwardly concave head portion, or cold end, of heat conducting material at a first end of the casing; a heat sink or hot end at a second end of the casing; and solid state electrothermal means within the casing in a heat exchanging relationship with the cold end and hot end and adapted to produce a subfreezing temperature at the head portion. The electrothermal means, or microcooler, is composed of an array of thermally consecutive thermoelectric and thermomagnetic cooling stages disposed so that the hot junction of the first stage is thermally adjacent the hot end of the instrument, and the cold junction of the first stage serves as a heat sink for the hot junction of the next stage. Each successive stage is most efficient in a progressively lower temperature range, and absorbs heat from the next consecutive stage. The last, or coldest, of the stages acts as a heat sink for, i.e. pumps heat from, the concave cold end of the instrument. For example, in a preferred embodiment, the microcooler includes a first Peltier effect means disposed as a heat sink for a second Peltier effect means having an applied magnetic field. The second Peltier effect means, in turn, is disposed as a heat sink for an Ettinghausen effect means disposed as a heat sink for the head portion.

The instrument may be of an implantable size i.e., approximately 5 centimeters in length, and may be implanted surgically, in the manner of a pacemaker or insulin pump, or through the use of a catheter or the like depending upon the location of the tumor.

The outwardly concave head portion of the instrument is thermally adjacent the final cold junction of the microcooler, and provides a directed and focused cooling effect upon the target tissue rather than the freezeball effect produced by the cryogenic probes which are known in the art. This allows the instrument to be implanted at the margin or edge of the tumor in the area of maximum vascular flow, with the coldfocusing head portion directed inwardly toward the center of the tumor to direct substantially all of the freezing effect toward the tumor and away from healthy tissue. The head portion may be detachable, and a plurality of head portions having varied shapes and sizes may be provided to provide maximum freezing effect upon different sizes and shapes of tumors. Moreover, the outer concave surface of the head portion may be provided with a loosely tangled fine metal filament in steel-wool form, providing continued contact with the instrument while the tumor changes size and shape as necrosis continues, yet allowing for good thermal contact between the head portion and the tumor.

The freezing effect is provided by a hybrid multistage thermoelectric-thermomagnetic cooling unit which reduces the temperature of the head portion of the instrument from body temperature (310° K.) to approximately 100° K. This temperature ensures that the temperature of the tissue in contact with the head portion is below 213° K.($-60°$ C.), the minimum temperature required for complete tumor necrosis. Each stage of the multi-stage cooling unit acts as a variable temperature heat sink for the next succeeding stage, and is operated in a temperature range which provides maximum cooling efficiency in terms of the electrical current consumed.

In a preferred example, a cascaded thermoelectric Peltier heat pump is provided to lower the temperature of the cold junction thereof from body temperature (310° K.) to approximately 190° K., which temperatures are within the most efficient range for the Peltier effect. The cold junction of the Peltier heat pump serves as a heat sink for a cascaded thermomagnetic heat pump connected thermally in parallel with the thermoelectric unit. The thermomagnetic unit is constructed by the application of a magnetic field across the thermocouples of a cascaded thermoelectric heat pump and, when operated in tandem with the aforementioned Peltier heat pump, is capable of efficiently reducing the temperature at its hot junction (194° K.) to 150° K. at its cold junction. The cold junction of the thermomagnetic system serves as a heat sink for an Ettingshausen cooling unit, which is capable of efficiently reducing the temperature at its hot junction (150° K.) to 100° K. which is then thermally conducted to the head portion of the instrument as described.

The cooling unit may be powered and controlled by one of the numerous methods and devices currently used for the operation of implantable electronic instruments. Electrical connectors may extend from the instrument through the skin to an external power source, or internal lithium batteries may be incorporated in the instrument as an internal power source which is externally controlled by a transcutaneously operated power switch incorporating a radio frequency control or other transcutaneous means. The instrument may also be powered by an internal nickel cadmium battery which may be recharged, and the instrument controlled, by radio frequency power transmitted from an external power source.

The instrument may be implanted surgically or otherwise placed with the concave head portion adjacent the edge of the target tumor area, and the temperature of the head portion is reduced from body temperature (310° K.) to 100° K. This temperature ensures the temperature of the tissue in contact with the head portion is below 213° K., the required temperature for necrosis. This temperature is maintained for a period of approximately four minutes, and the current to the instrument is then disconnected allowing a slow, spontaneous thawing for a period of 48 hours. During this period, the necrotic tissue, previously frozen, disintegrates and is carried away by body processes. A second freezing cycle is then begun to similarly treat the next layer of tumor tissue.

The implantable hypothermia instrument and method of the present invention provides numerous freeze-thaw cycles, thus allowing for complete necrosis of large and deep-seated tumors without repetitive invasive procedures. The instrument provides an optimal freezing rate of 120° C. per minute. The exact localization and focusing of the freezing ensures preservation of the healthy tissue adjacent to the tumor. As a result of the in-situ tumor necrosis, there is an enhancement in the tumor-specific immunity to subsequent tumor growth as a result of the prolonged exposure of the host to tumor antigen provided by the in situ necrosis. Further, the risks of metastasis as well as hermorrhaging are substantially limited as compared to extirpative surgery.

DETAILED DESCRIPTION

Figure 1:
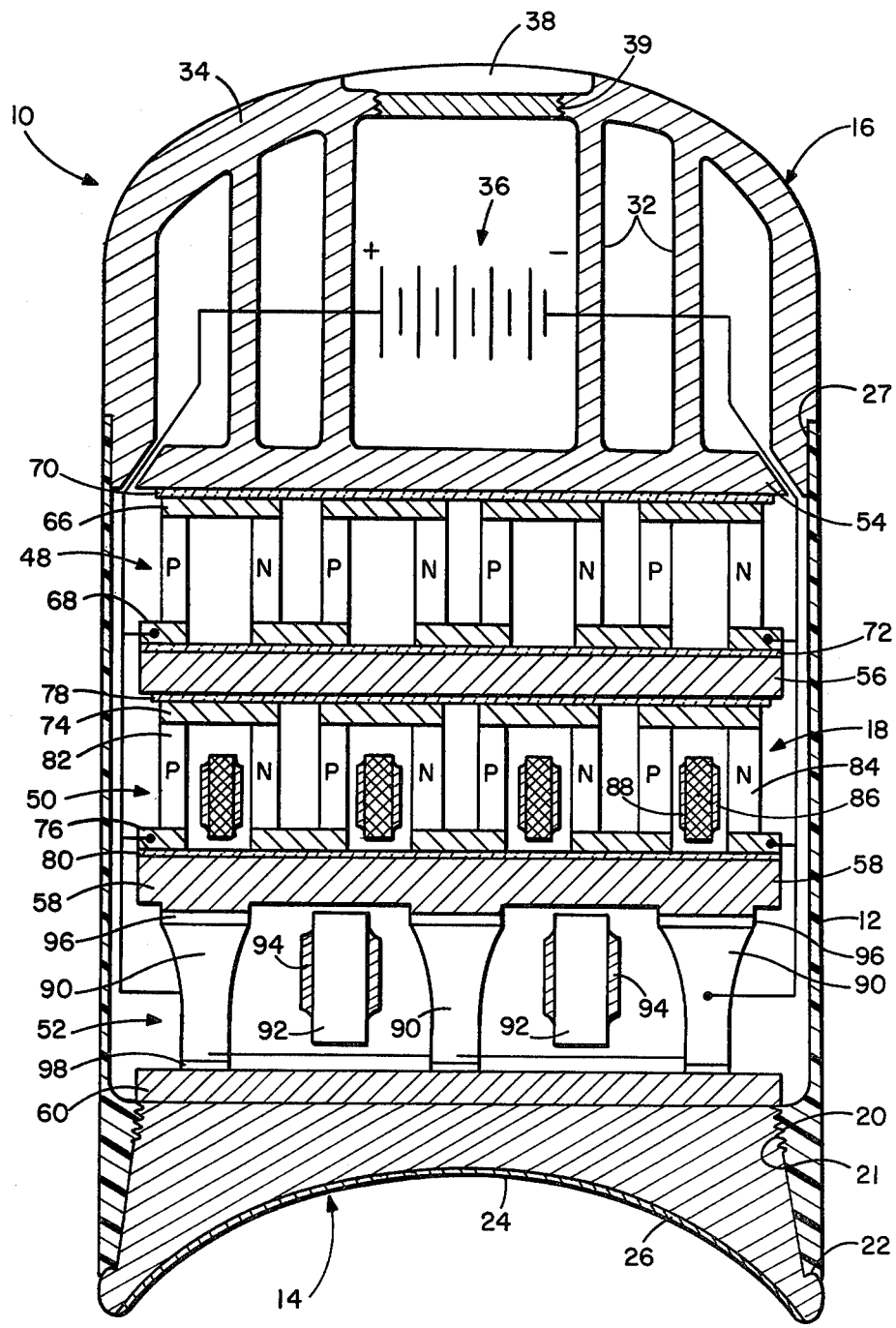
FIG. 1 is a schematic cross-sectional view of a hypothermia instrument in accordance with the present invention.
Figure 2:
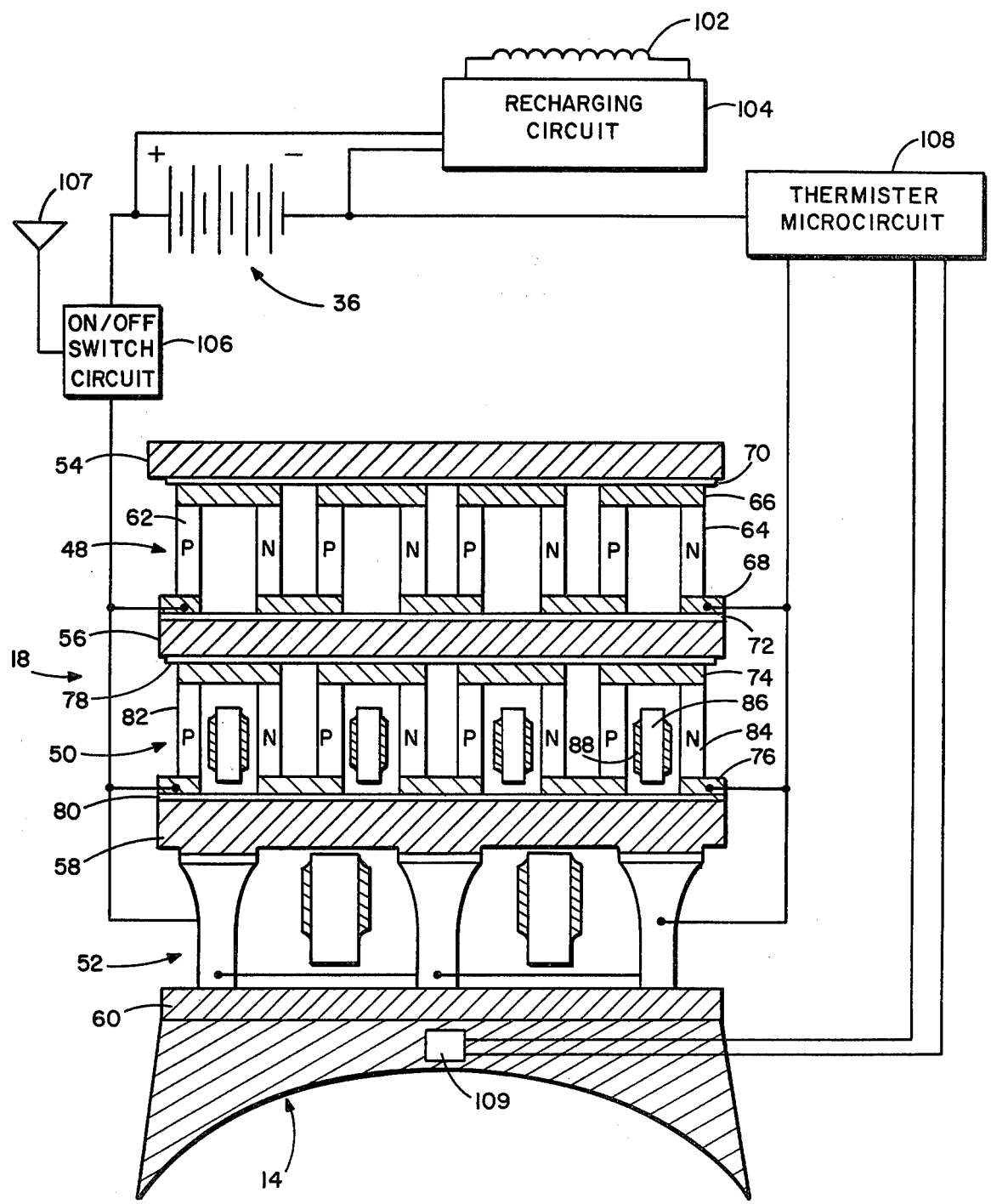
FIG. 2 is a schematic cross-sectional view of an alternative embodiment in accordance with the present invention.
Figure 3:
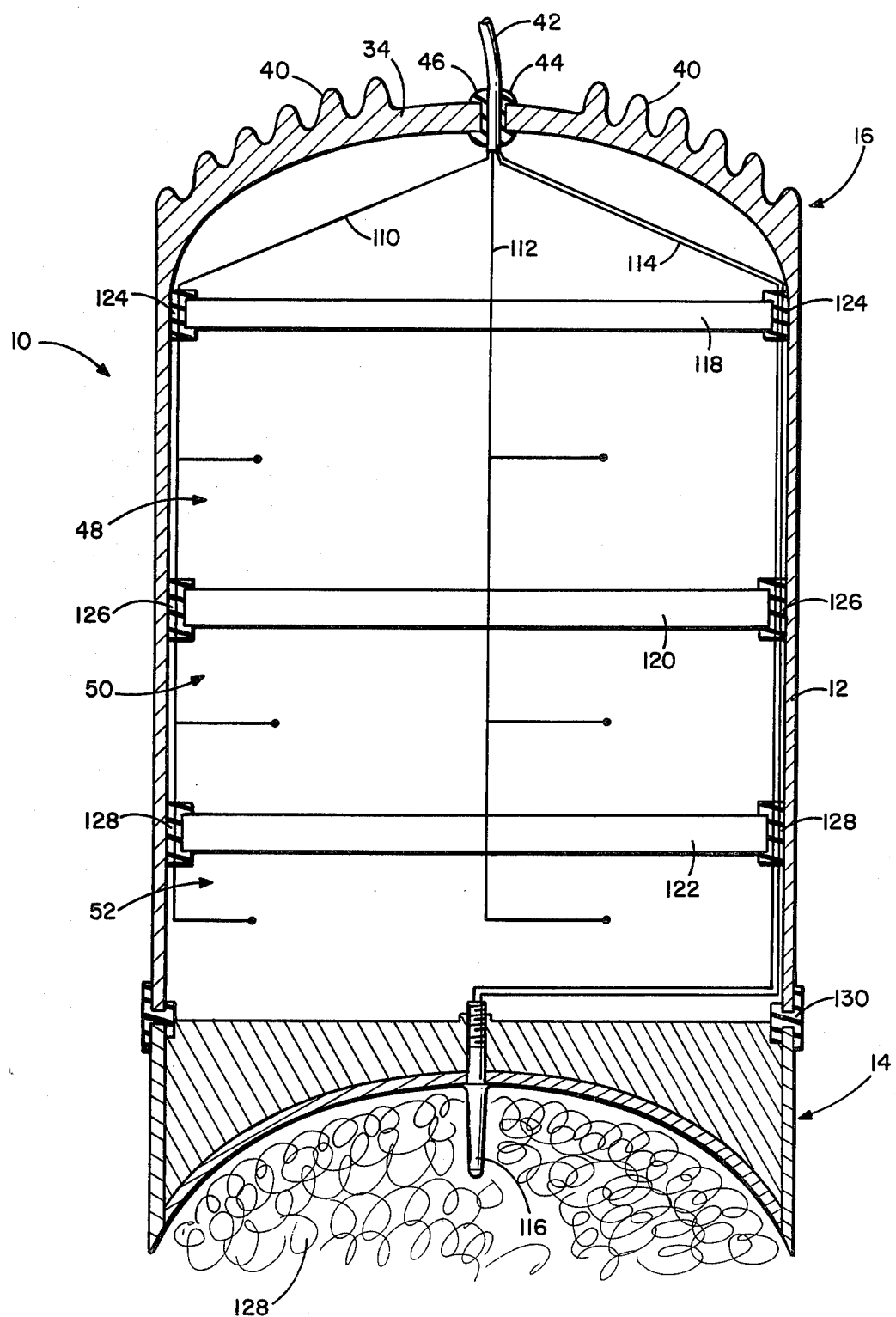
FIG. 3 is a schematic cross-sectional view of an alternative embodiment to that of FIG. 1.

By way of introduction, a hypothermia instrument 10, adapted for surgical insertion in the human body, is shown in FIGS. 1-3.

In FIG. 1, the hypothermia instrument 10 is shown to be cylindrical in form, and to have a casing 12 defining the major portion of the instrument. The casing 12 may be formed from a biocompatible material having a coefficient of thermal expansion appropriate for the temperature gradients herein described. Preferably, the casing 12 may be made from any one of a number of polymeric materials, such as epoxy, which have the advantage of providing thermal and electrical insulation properties. Other appropriate materials for the casing 12 would be stainless steel or silver, when provided with additional insulation means as set forth hereinafter.

In FIG. 1, the instrument 10 is further seen to include a concave head portion 14 at a first end thereof, a heat sink portion 16 disposed at a second end opposite said head portion 14 and a microcooler 18 disposed therebetween.

In FIG. 1, the head portion 14 is seen to be removably attached to the casing 12 by means of mating threaded portions 20 and 21 which, upon engagement, cause the head portion 14 and the casing 12 to be drawn into an abutting and sealing relationship at the flange 22 of the head portion 14. The head portion 14 is further seen to include an outwardly concave tumor abutting portion 24, said head portion 14 being detachable by means of the threads 20 and 21 to allow the substitution of additional head portions, not shown, having varied concave shapes adapted to fit the size and shape of the individual tumor, not shown. The head portion 14 is constructed of a material having high thermal conductivity such as silver or stainless steel, and is seen to include, along the tumor abutting portion 24, a film of fluorocarbon material 26 such as Teflon to serve as an anticryoadhesion material to prevent the risk of induced hemorrhaging upon the movement of the instrument in the treatment of a large target area of the tumor.

The heat sink 16 is shown to be joined to the casing 12 by epoxy adhesive at the junction 27 therebetween, although the heat sink 16 may be removably attached to the casing 12 by mating threads, not shown, similar to the threads 20 and 21.

Turning now to FIG. 3, the head portion 14 is shown to be faced with a woven wire cloth 128 in a tangled steel-wool form, allowing for good thermal contact between the head portion 14 and the changing size and shape of the tumor during treatment. Further with regard to FIG. 3, the head portion 14 is seen to be attached to and insulated from the casing 12, here represented as having been fashioned from a thermally conductive material such as stainless steel or silver, by a thermally insulative gasket member 30. The gasket member 30 is seen to join the head portion 14 and the casing 12 by means of a suitable low temperature adhesive such as epoxy.

As shown in FIG. 1, the instrument 10 includes a heat sink 16 for the transmission of heat generated by the microcooler 18. The heat sink 16 is constructed from a material having high thermal conductivity such as that used in the head portion 14. The struts 32 aid in the transmission of heat from the microcooler 18 to the outer portion 34 of the heat sink 16, where it is there transmitted to healthy tissue, not shown, surrounding the instrument 10. The heat sink 16 may also include a battery 36 to supply power to the microcooler as hereinafter described, and is shown to include an end cap 38, removable via threads 39, in the outer portion 34 to provide access to the battery 36 for maintenance and replacement thereof. In addition to the struts 32, or as substitutes therefor, the heat sink 16 may be filled with a thermal conducting fluorocarbon liquid such as polyfluorinated polyethers having the general formula

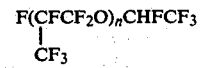

where n is a whole number in the range of 1-11. These materials are available from E.I. DuPont de Nemours & Co.

Turning now again to FIG. 3, the heat sink 16 is seen to include optional heat radiating fins 40 disposed about the outer portion 34 to assist in the transfer of heat therefrom. The casing 12, here shown to be made of a thermally conductive material and insulated from the head portion 14 by the gasket 30, serves as an additional heat radiating member.

The instrument 10 described in FIG. 3 is seen to be operated and powered by an external power source, not shown, rather than by the battery 36 as shown in FIG. 1. Electrical current enters the instrument 10 through a Teflon coated power cord 42, passing through a grommet 44 contained in an opening 46 formed in the outer portion 34 of the heat sink 16.

Turning now to FIGS. 1 and 2, the microcooler 18 will be described in detail. Due to the requirement of a freeze rate of 120° C. per minute and a desired tissue temperature of 213° K., the microcooler 18 must cool the head portion 14 across a temperature gradient of 210° K. from 310° K. (body temperature) to 100° K. According to the present invention, these requirements are met through the use of a thermoelectric Peltier section 48, a thermomagnetic section 50 and a third section 52 which employs the Ettingshausen effect. Each of the three sections is utilized in a particular portion of the temperature gradient over which it pumps heat in an effective and efficient manner. The Peltier section 48, having a hot junction 54 cooled by the heat sink 16, reduces the temperature of the heat sink 16 from body temperature (310° K.) to approximately 194° K. at its cold junction 56. The cold junction 56 and thus the Peltier section 48, serves as a heat sink for the thermomagnetic section 50 which reduces the temperature of the junction 56 from 195° K. to 150° K. at the junction 58. In turn, the junction 58, and thus the thermomagnetic unit 50, serves as a heat sink for the Ettingshausen unit 52 which further reduces the temperature of the junction 58 i.e. 150° K., to a temperature of 100° K. at a cold junction 60, which temperature is then thermally conducted to the head portion 14.

The mechanism of thermoelectric cooling, known as the Peltier effect, is well known, and since the refinement of semiconductor materials thermoelectric refrigeration has become increasingly common. Semiconductor materials with dissimilar characteristics are connected electrically in series and thermally in parallel, so that two junctions are created. The semiconductor materials are n- and p-type and are so named because either they have more electrons than necessary to complete a perfect molecular lattice structure (n-type) or not enough electrons to complete a lattice structure (p-type). The extra electrons in the n-type materials and the holes left in the p-type material are called carriers and they are the agents that move the heat energy from the cold to the hot junction. Heat absorbed at the cold junction is pumped to the hot junction at a rate proportional to the carrier current passing through the circuit and the number of couples.

Couples are combined in a module where they are connected in series electrically and in parallel thermally. A single stage module is capable of pumping heat where the difference in a temperature of the cold junction and hot junction ($\Delta T$) is 70° C. or less. In applications which require higher $\Delta T$'s, such as here, the modules in tiers can be cascaded i.e., the mechanical stacking of modules in tiers so that the cold junction of one module becomes the heat sink for a smaller module on top. In addition to the heat pumped by any given tier, the next lower tier must also pump the heat resulting from the input power to the upper tier. Consequently, each succeeding tier must be larger and larger from the top of the cascade downward toward the hot junction.

In the instrument 10, a six-tier cascaded Peltier effect heat pump, employing $Bi_2Te_3(p)$—$Bi_2Te_3(n)$ alloy, such as manufactured by Cambridge Thermionic Corporation under the trademark CAMBION, provides a $\Delta T$ of 115° K. as required by the microcooler 18.

The Peltier unit 48 is seen to comprise alternating p-type $Be_2Te_3$ semiconductors 62 and n-type $Be_2Te_3$ semiconductors 64 and metal p—n connectors 66 and 68 which are electrically insulated from the junctions 54 and 56 by electrical insulation members 70 and 72, respectively. Alternatively, the junctions 54 and 56 may be made of ceramic material which has electrical insulation and thermal conducting properties, whereupon the electrical insulation members 70 and 72 may be omitted.

Methods for the production of solid state thermoelectric coolers are known in the art and coolers of the type represented figuratively by Peltier unit 48 in FIGS. 1 and 2 are available from one of numerous commercial suppliers, as hereinbefore described.

The six-tier cascaded solid state thermoelectric Peltier unit 48, by providing a temperature of 195° K. at junction 56, serves as a heat sink for the second, thermomagnetic stage 50 of the microcooler 18. The thermomagnetic stage 50 is constructed in a manner similar to that of the thermoelectric stage 48 and includes metal connecting strips 74 and 76 as well as electrical insulating means 78 and 80, respectively, between the respective connecting strips 74 and 76 and the heat junctions 56 and 58. The thermomagnetic unit 50 employs thermocouples of Bi—Sb alloy which are doped to provide p-type semiconductors 82 and n-type semiconductors 84.

The thermomagnetic stage 50 is preferably a three tier cascaded module, as hereinbefore described, which operates in an applied magnetic field of 3000 to 8000 gauss to improve the thermocouple efficiency over a colder portion of the temperature gradient. Preferably, the magnetic field is provided by samariumcobalt permanent magnets 86, having soft iron fieldforming pole faces 88, placed in spaces between the thermocouple elements.

The magnets 86 provide a transverse magnetic field on the thermocouple elements and allow the thermomagnetic stage to operate efficiently in a reduced temperature range and to produce at the junction 58 a temperature of 150° K.

Figure 4:
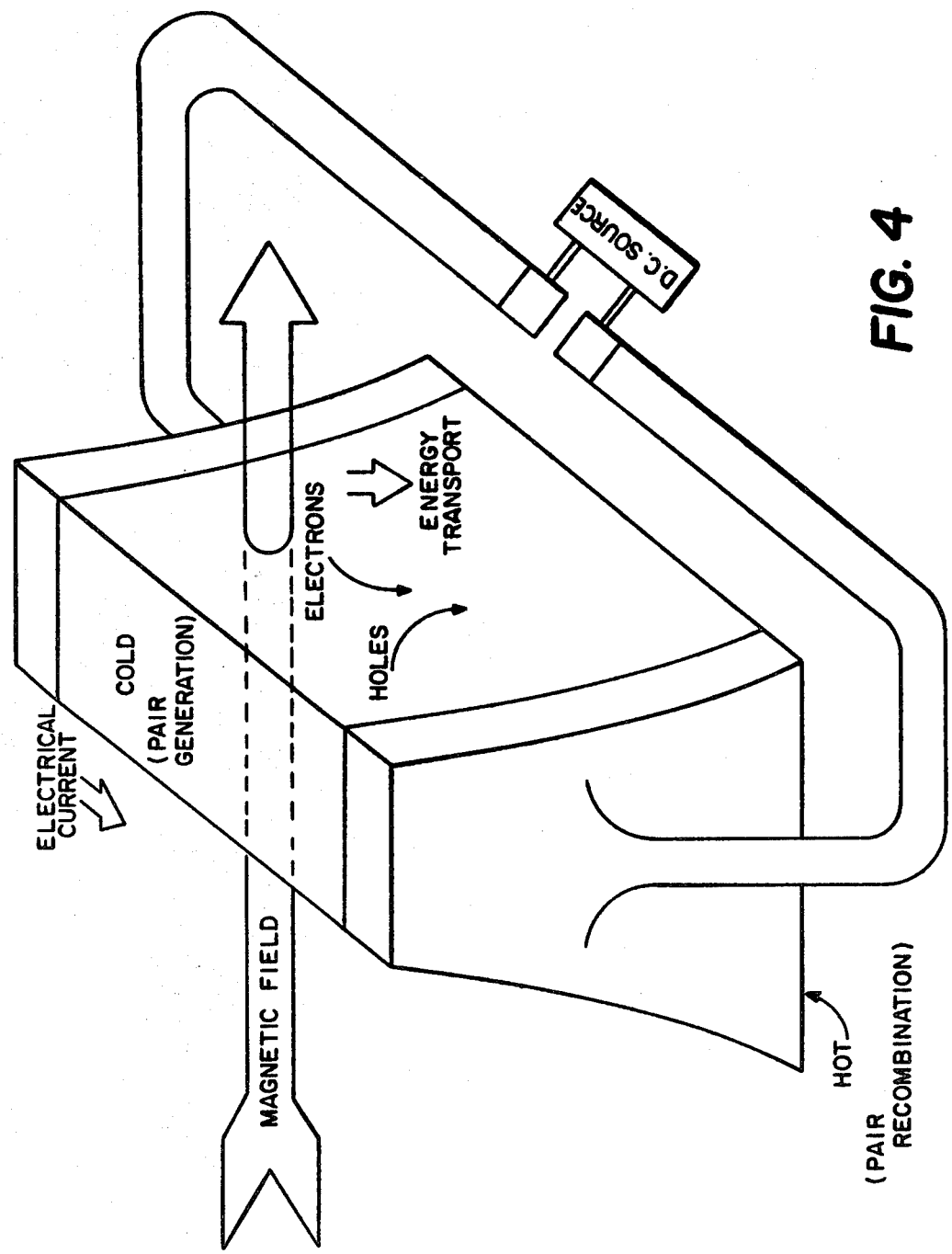
FIG. 4 is a schematic representation of an Ettingshausen parallelpiped.

The last cooling stage of the microcooler 18 is provided by a cooling unit 52 which employs the Ettingshausen effect. The Ettingshausen effect is described with reference to FIG. 4, and occurs when a current passes through a parallelpiped of intrinsic (n=p) material. A transverse magnetic field deflects the carriers and the net carrier transport creates an energy flow since the carriers must recombine (heating) on one side and be generated (cooling) on the other side.

The Ettingshausen cooler is preferably constructed from optimally doped n-type Bi—Sb alloys, in which the thermomagnetic effects are largest in the temperature range of 100° K.-200° K. The $\Delta T$ across the Ettingshausen cooler saturates at a critical value of the magnetic field which depends upon temperature. The condition for saturation is that the product of the charge carrier mobility in the magnetic field be much greater than unity. As the mobility falls with increasing temperature, the magnetic field required to produce saturation becomes very large at high temperatures. The thermoelectric stage 48 and the thermo magnetic stage 50, in turn, provide a heat sink for the Ettingshausen cooler which will limit the saturation field to reasonable values and allow the cooler to operate in a temperature range which will yield the largest $\Delta T$, or the lowest overall temperature at the head piece 14.

Figure 5:
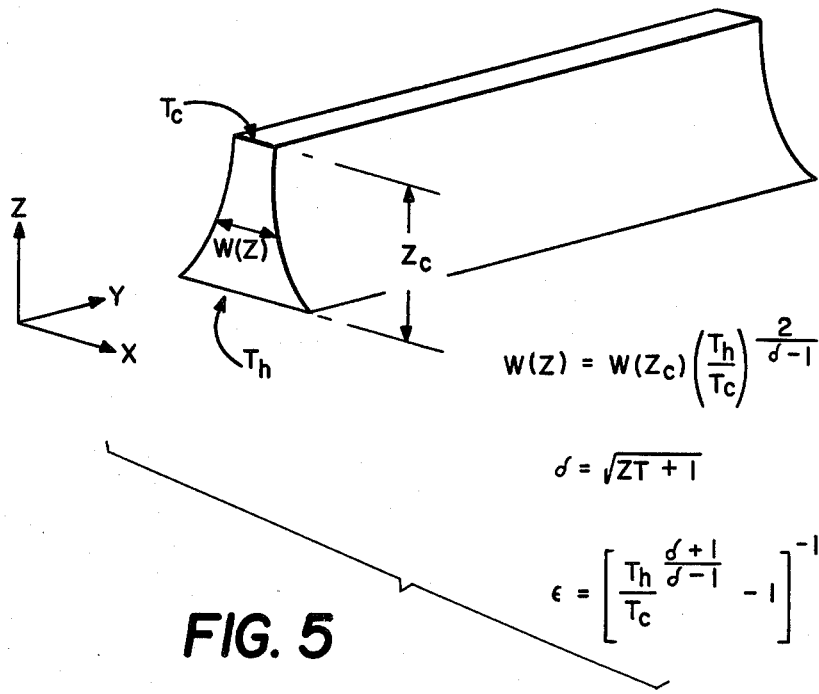
FIG. 5 is a representation of an exponentially shaped Ettingshausen parallelpiped.

As hereinbefore described, thermoelectric couples may be cascaded to improve the performance above that of a single couple. Similarly, the Ettingshausen device, comprising a single unit 90, is cascaded by the shaping of the single element exponentially as described in FIG. 5. Experimentally, shaped devices have more than doubled the performance of a simple parallelpiped.

The required magnetic field of 3000 to 8000 gauss in the Ettingshausen unit 52 is provided by small, lightweight samarium-cobalt magnets 92 placed between the Ettingshausen devices 90 as shown in FIGS. 1 and 2. In a manner similar to the magnets of the thermomagnetic stage 50, the magnets 92 are provided with soft iron field forming pole faces 94 to provide the required transverse magnetic field. The individual Ettingshausen devices 90 are seen to be mounted between the junctions 58 and 60 and separated therefrom by means of electrically insulating and thermally conductive material 96 and 98.

Figure 6:
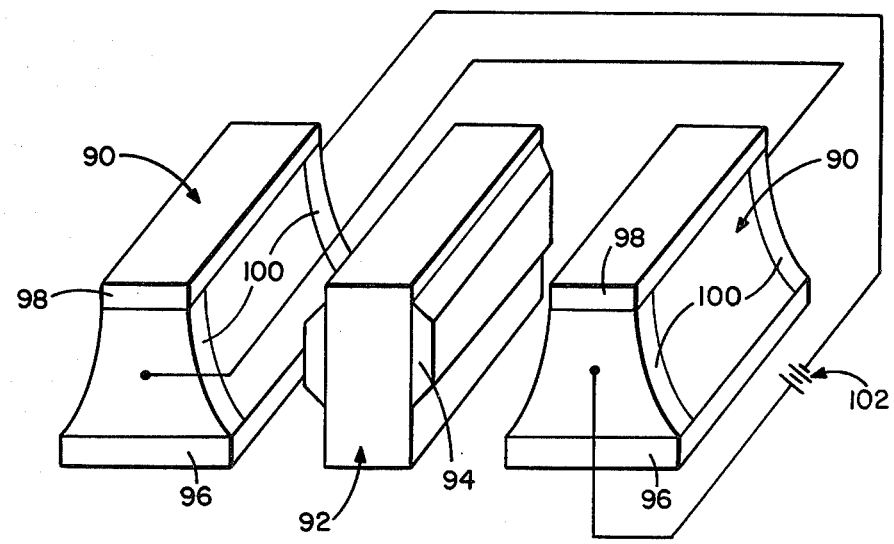
FIG. 6 is a schematic representation of a portion of the Ettingshausen cooler of the present invention.

Turning now to FIG. 6, two of the Ettingshausen devices 90 are seen to be mounted, figuratively, on either side of the samarium-cobalt magnet 92. The Ettingshausen devices are seen to include electrically conductive metal pole end pieces 100 and the electrically insulative and thermally conductive pieces 96 and 98. The devices 90 are seen to be connected to the battery 102.

In another embodiment, electromagnetic coils are placed in the spaces between the Ettingshausen devices 90 as well as in the spaces between the n and p couples 82 and 84 in the thermomagnetic section 50 as hereinbefore described. The electric current which flows through the Ettingshausen units 90 and the electromagnetic section 50 is also passed through the coils to produce the required magnetic field. The number of turns in the coil is such that a field of 8K Gauss is produced. The coil is positioned in such a way that the magnetic field which it produces is directed in a direction perpendicular to the direction of current flow in the Ettingshausen units and in the thermomagnetic elements.

Calculations were performed in order to determine the amount of power required by the hypothermia instrument 10. The first part of these calculations involved developing an expression for the optimal values of the intermediate temperatures for each stage of the instrument. This calculation produced the following set of values for the intermediate cascading stages:

A. An exponentially shaped Ettingshausen stage which will take a load from 100° K. to 150° K.

B. Three stages of a thermomagnetic unit having the following values of temperature:
$T_{m0} = 150°$ K.
$T_{m1} = 163.43°$ K.
$T_{m2} = 178°$ K.
$T_{m3} = 194°$ K.

C. Six stages of a thermoelectric unit having the following values of temperature:
$T_{e0} = 194°$ K.
$T_{e1} = 209.76°$ K.
$T_{e2} = 226.8°$ K.
$T_{e3} = 245.22°$ K.
$T_{e4} = 265.15°$ K.
$T_{e5} = 286.69°$ K.
$T_{e6} = 310°$ K.

In order to calculate the power requirements of the instrument 10, the following assumptions were made:

A. The heat load on the probe of the instrument at the cold stage is 10mW;

B. For the Ettingshausen unit, the figure of merit is $Z' = 2.5 \times 10^{-3}$°K$^{-1}$;

C. The figure of merit for the thermomagnetic unit 50 is $Z_m = 5 \times 10^{-3}$ K$^{-1}$;

D. The figure of merit for the thermoelectric unit 48 is $Z_e = 3 \times 10^{-3}$°K$^{-1}$.

With the above assumptions, the following results for the power requirement of each stage were computed according to the following formulae and are shown in Table I.

$$\bar{T} = \tfrac{1}{2}(T_H + T_C)$$

$T_H =$ Hot temperature
$T_C =$ Cold temperature

For the Ettingshausen stage, the efficiency of the exponentially shaped device is:

$$\epsilon' = \{(T_H/T_C)^{1/n'} - 1\}^{-1}$$

$$n' = \frac{1 - \delta'}{1 + \delta'}$$

$$\delta' = \sqrt{1 - Z'\bar{T}}$$

$$P_{ET} = Q_c/\epsilon'$$

$Q_c =$ Heat pumped from cold reservoirs.

For the thermomagnetic stage, the efficiency is:

$$\epsilon_{TM} = \frac{T_C}{\Delta T} \frac{\delta_m - (T_H/T_C)}{1 + \delta_m}$$

$$\delta_m = \sqrt{1 + Z_m \bar{T}}$$

$$\Delta T = T_H - T_C$$

This calculation has to be performed for each stage using the proper values of $\Delta T$, $T_H$ and $T_C$ for each stage. For example, $$\epsilon'_{TM} = M_1 = \frac{T_0}{T_1 - T_0} \frac{\delta_m{}^1 - T_1/T_0}{1 + \delta_m{}'}$$

$$\delta_m{}' = \sqrt{1 + Z_m \bar{T}_1}$$

$$\bar{T}_1 = \tfrac{1}{2}(T_0 + T_1)$$

$$P_{Mi} = \frac{Q_{Mi}}{\epsilon_{TMi}}$$

$$Q_{Mi} = P_{M(i-1)} + Q_{M(i-1)}$$

For the Peltier stages:

$$\epsilon_E = \frac{T_C}{\Delta T} \frac{\delta_e - (T_H/T_C)^{22}}{1 + \delta_e}$$

$$\delta_e = \sqrt{1 + Z_e \bar{T}}$$

This calculation again has to be performed for each state using the proper values of $\Delta T$, $T_H$ and $T_C$ for each stage.

For example, $$\epsilon_{E2} = E_2 = \frac{T_1}{T_2 - T_1} \frac{\delta_2 - T_2/T_1}{1 + \delta_2}$$

-continued $$\delta_2 = \sqrt{1 + Z_e \overline{T_2}}$$

$$\overline{T_2} = \frac{1}{2}(T_2 + T_1)$$

$$P_{Ei} = \frac{Q_{Ei}}{\epsilon_{Ei}}$$

$$Q_{Ei} = Q_{E(i-1)} + P_{E(i-1)}$$

TABLE I

| Stage | Efficiency | Heat Output mw | Power Required mw |
|---|---|---|---|
| ET | 0.9097 | 20.993 | 10.993 |
| M1 | 1.174 | 38.875 | 17.882 |
| M2 | 1.294 | 68.917 | 30.042 |
| M3 | 1.393 | 118.387 | 49.47 |
| E1 | 1.01 | 235.6 | 117.21 |
| E2 | 1.104 | 449.03 | 213.43 |
| E3 | 1.205 | 821.67 | 372.64 |
| E4 | 1.309 | 1449.49 | 627.82 |
| E5 | 1.418 | 2471.7 | 1022.21 |
| E6 | 1.53 | 4087.2 | 1615.49 |

This table indicates that under the conditions of the calculation, the power required is 4077.2mW i.e. just above 4 watts. Allowing for a 400% safety factor, the power requirement in practice for the instrument 10 would be 16 watts. As thermoelectric devices are preferably high current-low voltage unit, the battery 36 must supply a current of about 8 amperes at a potential of 2 volts.

Returning now to FIG. 2, the control and operation of the hypothermia instrument 10 will be further detailed. The microcooler 18 is seen to be powered by a battery 36, in this instance a rechargeable nickel cadmium battery. The battery 36 is recharged via radio frequency power transmitted from an external portable source, not shown, and received by a coil 102, by means of a recharging circuit 104. The battery pack 36 may be "quick charged" at 40mA in about 2½hours. This system, more fully described hereinafter, will charge implanted batteries through 13 mm tissue thickness, using 50mm diameter transmitting and receiving coils. The microcooler 18 is switched off during recharging, and operated to produce the freeze/thaw cycles described herein, by an on-off switch circuit 106 which is controlled, through an implanted antenna 107, by an external radio transmitter, not shown.

The radio-controlled devices are described in detail by Jeutter in *IEEE Transactions On Biomedical Engineering*, Vol. BME-29, No. 5, May 1982, which is hereby incorporated by reference.

The temperature produced by the microcooler 18 at the head portion 14 is controlled by a thermistor microcircuit 108. The microcircuit 108 receives voltage from a silicone diode cryogenic temperature sensor 109 which passes increasing voltage as the temperature of the sensor decreases. For example, a silicone diode cryogenic temperature sensor may pass 0.3 volts at room temperature, 2.5 volts at helium temperatures and show a temperature sensitivity of approximately 50 millivolts per degree Kelvin. Such sensors are available from Lake Shore Cryotronics, Inc. The voltage produced by the sensor 109 is employed, by the thermistor microcircuit 108 in a manner known in the art, to maintain the proper temperature in the head piece 14 during the freeze/thaw cycles hereinafter described.

Turning now to FIG. 3, yet another embodiment of the present invention shows the electric current for the operation of the instrument 10 entering the heat sink 16 via a Teflon-coated stainless steel or copper control cable 42. Contained in the control cable 42 are power wires 110 and 112 which connect the thermoelectric stage 48, the thermomagnetic stage 50 and the Ettingshausen stage 52 to an external power source and power switch, neither shown. Also contained in the cable 42 are leads 114 from the silicone diode cryogenic temperature sensor 116, which feeds voltage to an external thermistor microcircuit, not shown, used to control the temperature of the head piece 14 as described. The sensor 116 is seen to protrude from the face of the head piece 14 to allow the direct sensing of the temperature of the tumor to be treated. It should further be noted that in FIG. 3 the instrument 10 also employs thermal junctions 118, 120 and 122, formed of ceramic material having high thermal conductivity and minimal electrical conductivity, thus obviating the need for the electrical insulating members 70, 72, 78, 80, 96 and 98 shown in FIG. 1. The junctions 118, 120 and 122 are thermally insulated from the casing 12 of the instrument 10 by elastomeric support members 124, 126, and 128, each of said support members having low thermal conductivity.

While the instrument 10 may be used to treat dermal and subdermal tumors or other diseased surface tissue, its primary utility is seen as the treatment of deep-seated tumors without repetitive invasive procedures. In this regard, the instrument 10 is implanted next to the tumor and positioned with the concave cold end 14 abutting the tumor margin by standard surgical techniques or through the use of a catheter when the tumor is within the lung, alimentary canal or genital-urinary tract. In this regard, the terms "implant" and "implantable" refer to the placement of the instrument within the body, whether by surgical or other techniques as described. Care should be taken to avoid the surgical invasion of the tumor in order to avoid the risk of metastatis. Preferably, the instrument 10 is positioned to allow external manipulation of the patient's body to reposition the instrument as the size of the tumor is reduced by necrosis.

If the instrument 10 is operated by implanted nickel cadmium batteries and the transcutaneous implanted battery recharging and power switching system hereinbefore described, the coil and antenna for the recharging and power switching system should be placed within the required distance below the skin i.e. 10 to 15mm tissue thickness for the charging unit and up to 100mm tissue thickness for the power switching system. If an external power and switching source, shown in FIG. 3, is used to operate the instrument 10, the Teflon-coated control cable 42 is led through the patient's skin to the external power source in the same manner as with other implantable instruments.

After implanting the instrument 10 and allowing for a reduction of swelling and other traumas attendant thereto, the current is caused to flow in the microcooler 18 until the temperature of the portion of the tumor adjacent the cold end 14 is reduced to at least 213° K. (−60° C.). This temperature may be ascertained by a tumor-penetrating sensor such as the sensor 116 in FIG. 3, or by allowing the cold end 14 to reach a predetermined temperature, depending upon the density of the tumor tissue, as determined by the sensor 109 as shown in FIG. 2. According to the present invention, this temperature is attained with a freezing rate of 120° C. per minute.

After the tissue reaches at least −60° C., this temperature is kept constant for three to four minutes. During this time period, the concave shape of the tumor abutting portion 24 of the cold end 14 focuses the freezing effect to form a sphere of frozen tissue adjacent the instrument 10. During the freezing cycle, the heat pumped from the cold end 14 is safely conducted to the healthy tissue by the heat sink 16.

After a frozen area of the desired size and temperature has been formed, the current to the instrument is then disconnected allowing for a slow, spontaneous thawing, and over a period of about 48 hours, the dead tumor tissue disintegrates and is carried away by body processes. The current is then switched on for another freeze/thaw cycle, and the next layer of tumor tissue is destroyed.

The hypothermia instrument of the present invention, and the method of its use, allows repeated and controlled freeze/thaw cycles for the total and complete necrosis of deep-seated tumors without repetitive invasive procedures. The instrument attains in-situ tumor necrosis, with the accompanying enhancement of the tumor-specific immunity to subsequent tumor growth which results from the prolonged exposure of the host to tumor antigen provided by in-situ tumor necrosis. Further, the instrument allows accurate and controlled temperature as well as rate of freezing and thawing. The freezing may be focused and localized to ensure the preservation of healthy tissue adjacent the tumor. In addition, the tumor necrosis may be induced without hemorrhaging or other trauma which would serve to induce metastisis of the tumor cells.

Although the foregoing invention has been described in some detail by way of illustration and example, changes in form and the substitution of equivalents are contemplated as circumstances may suggest or render expedient. For example, while the instrument has been described as being cylindrical in form, hemispherical or other shapes may be desired or dictated by the intended use. Although specific terms have been employed herein, they are intended in a descriptive sense and not for purposes of limitation, the scope of the invention being delineated in the following claims.

What is claimed is:

1. A hypothermia instrument for the application of cytostatic freezing temperatures to selected portions of the body, said instrument comprising:
    an outer casing;
    an outwardly concave cold end of heat conducting material at a first end of the casing;
    a hot end of heat conducting material at a second end of the casing opposite the first end;
    an array of thermally consecutive cooling means having serially increasing cooling ability disposed between the hot end and the cold end, the hot end serving as a heat sink for a thermoelectric Peltier first cooling means, said first cooling means serving as a heat sink for a thermoelectric-thermomagnetic Peltier second cooling means, said second cooling means serving as a heat sink for a thermomagnetic Ettingshausen third cooling means, the third cooling means serving as a heat sink for the cold end and pumping heat therefrom through the preceding cooling means to the hot end;
    means providing electric current to said array and means for interrupting said current,
    said array being capable of producing a cold end temperature of about 100° kelvin.

2. An instrument according to claim 1 which is constructed of biocompatible material and is implantable in the body, and wherein the thermoelectric Peltier first cooling means is capable of providing a temperature of about 190° kelvin, the thermoelectric-thermomagnetic secon cooling means is capable of providing a temperature of about 150° kelvin, and the thermomagnetic Ettingshausen third cooling means is capable of providing a temperature of about 100° kelvin.

3. An instrument according to claim 2 wherein the current for the array of cooling means is provided by a battery contained in said hot end.

4. An instrument according to claim 2 which further includes a temperature sensing means extending from the outwardly concave cold end to determine the temperature produced within the selected body portion.

5. A hypothermia instrument for the application of cytostatic freezing temperatures to selected portions of the body, said instrument comprising an outer casing; an outwardly concave head portion of heat-conducting material; solid state cooling means with said casing in a heat-exchanging relationship with the head portion and adapted to produce a sub-freezing temperature at said head portion, said cooling means including a first Peltier effect means disposed as a heat sink for a second Peltier effect means having a first applied magnetic field thereacross, said second Peltier means disposed as a heat sink for an Ettingshausen effect means including a second applied magnetic field thereacross, the Ettingshausen effect means disposed as a heat sink for said head portion; and means providing electric current to the cooling means and means for interrupting said current.

6. An instrument according to claim 5, wherein the first cooling means is capable of producing a temperature of about 190° delvin at a hot end of the second cooling means which, in turn, is capable of producing a temperature of about 150° kelvin at a hot end of the third cooling means which in turn, is capable of producing a temperature of about 100° kelvin at the head portion.

7. An instrument according to claim 6 wherein current for the array of cooling means is provided by a battery contained in said hot end.

8. An instrument according to claim 6, which further includes a temperature sensing means extending form the outwardly concave head portion, said sensing means adapted to determine the temperature produced within the selected body portion.

9. A method for the in-situ necrosis of a tumor in a body, comprising the steps of;
    providing an instrument comprising an outer casing with an outwardly concave cold end of heat conducting material at a first end thereof and a hot end of heat conducting material at a second end of the casing, with an array of thermally consecutive cooling means disposed between the hot end and the cold end with serially increasing freezing ability, wherein the hot end serves as a heat sink for a thermoelectric Peltier first cooling means, the first cooling means serves as a heat sink for a thermoelectric-thermomagnetic Peltier second cooling means and the second cooling means serves as a heat sink for a thermomagnetic Ettingshausen third cooling means, with the third cooling means in turn serving as a heat sink for the cold end and pumping heat therefrom to the hot end, and means providing electric current to said array and means for interrupting said current;

implanting said instrument in the body with the concavity of the cold end adjacent to and facing the tumor;

allowing current to flow for a time sufficient to cause a portion of the tumor to be frozen and reduced to a temperature of at least 213° kelvin;

interrupting the current for a time sufficient to cause said portion to thaw and to allow necrotic tissue formed by the freezing to be carried away by body processes; and repeating the allowing and interrupting steps.

10. The method of claim 9 wherein the first cooling means provides a temperature of about 190° kelvin, the second cooling means provides a temperature of about 150° kelvin, and the third cooling means provides a temperature of about 100° kelvin.

11. A method for the in-situ necrosis of a tumor in the body, comprising the steps of:

providing an instrument comprising an outer casing, an outwardly concave head portion of heat conducting material and cooling means within said casing in a heat exchanging relationship with the head portion and adapted to produce a sub-freezing temperature, said cooling means including a first Peltier effect means disposed as a heat sink for and providing a temperature of about 190° kelvin to a hot end of a second Peltier effect means having a first applied magnetic field thereacross, said second Peltier means disposed as a heat sink of r and providing a temperature of about 150° kelvin to a hot end of an Ettingshausen effect means including a second applied magnetic field thereacross, wherein the Ettingshausen effect means serves as a heat sink for and provides a temperature of about 100° kelvin to said head portion, and means providing electric current to the cooling means and means for interrupting said current;

implanting the instrument in the body with the concavity of the head portion adjacent to and facing the tumor;

allowing current to flow for a time sufficient to allow a portion of the tumor to be frozen and reduced to a temperature of at least 213° kelvin;

interrupting the current for a time sufficient to allow necrotic tissue formed by the freezing to thaw; and repeating the allowing and interrupting steps.

* * * * *